(12) United States Patent
Orsak et al.

(10) Patent No.: US 11,382,677 B2
(45) Date of Patent: Jul. 12, 2022

(54) CHARCO-RESIS IMPLANT, ALIGNMENT INSTRUMENT, SYSTEM AND METHOD OF USE

(71) Applicant: James Orsak, East Ridge, TN (US)

(72) Inventors: James Orsak, East Ridge, TN (US); Frank Bono, Castle Rock, CO (US); Spanky Raymond, Uniontown, OH (US)

(73) Assignee: James Orsak, East Ridge, TN (US)

( * ) Notice: Subject to any disclaimer, the term of this patent is extended or adjusted under 35 U.S.C. 154(b) by 243 days.

(21) Appl. No.: 16/735,270

(22) Filed: Jan. 6, 2020

(65) Prior Publication Data

US 2020/0146736 A1    May 14, 2020

Related U.S. Application Data

(63) Continuation of application No. 14/379,361, filed as application No. PCT/US2013/026397 on Feb. 15, 2013, now Pat. No. 10,524,845.
(Continued)

(51) Int. Cl.
| | |
|---|---|
| *A61B 17/17* | (2006.01) |
| *A61B 17/72* | (2006.01) |

(Continued)

(52) U.S. Cl.
CPC ...... *A61B 17/8685* (2013.01); *A61B 17/1775* (2016.11); *A61B 17/68* (2013.01);
(Continued)

(58) Field of Classification Search
CPC . A61B 17/861; A61B 17/8625; A61B 17/864; A61B 17/8685; A61B 17/8872; A61B 17/90; A61B 2017/564; A61B 2017/681; A61B 17/1775; A61B 17/68; A61B 17/7291; A61F 2002/30405;
(Continued)

(56) References Cited

U.S. PATENT DOCUMENTS

| | | |
|---|---|---|
| 4,781,182 A | 11/1988 | Purnell |
| 5,019,079 A | 5/1991 | Ross |

(Continued)

OTHER PUBLICATIONS

International Search Report and Written Opinion of the International Searching Authority for PCT/US2013/026397, dated Jun. 13, 2013, 10 pages.
(Continued)

*Primary Examiner* — Samuel S Hanna
(74) *Attorney, Agent, or Firm* — Heslin Rothenberg Farley & Mesiti P.C.; Jacquelyn A Graff, Esq.

(57) ABSTRACT

An implant system, alignment guide, bone fusion system and surgical method for correction of a flat foot or rocker-bottom deformity, such as a Charcot foot. The implant system includes a bone implant and an elongate member. The bone implant includes a proximal end, a distal end, a hole along a longitudinal axis, and at least one opening intersecting the hole. The elongate member includes a first end with a head portion, a second end with a coupling mechanism, and an opening along a longitudinal axis. The coupling mechanism of the elongate member engages the at least one opening to couple the bone implant to the elongate member.

19 Claims, 14 Drawing Sheets

Related U.S. Application Data

(60) Provisional application No. 61/599,604, filed on Feb. 16, 2012.

(51) Int. Cl.

| | | |
|---|---|---|
| *A61B 17/56* | (2006.01) | |
| *A61B 17/86* | (2006.01) | |
| *A61B 17/68* | (2006.01) | |
| *A61F 2/42* | (2006.01) | |
| *A61F 2/46* | (2006.01) | |
| *A61B 17/88* | (2006.01) | |
| *A61F 2/30* | (2006.01) | |
| *A61B 17/90* | (2006.01) | |

(52) U.S. Cl.
CPC .......... *A61B 17/861* (2013.01); *A61B 17/864* (2013.01); *A61B 17/8625* (2013.01); *A61B 17/8872* (2013.01); *A61F 2/4202* (2013.01); *A61F 2/4606* (2013.01); *A61B 17/7291* (2013.01); *A61B 17/90* (2021.08); *A61B 2017/564* (2013.01); *A61B 2017/681* (2013.01); *A61F 2002/30405* (2013.01); *A61F 2002/4223* (2013.01); *A61F 2002/4238* (2013.01); *A61F 2002/4628* (2013.01); *A61F 2002/4687* (2013.01)

(58) Field of Classification Search
CPC ...... A61F 2002/4223; A61F 2002/4238; A61F 2002/4628; A61F 2002/4687; A61F 2/4202; A61F 2/4606
See application file for complete search history.

(56) References Cited

U.S. PATENT DOCUMENTS

| | | |
|---|---|---|
| 6,517,541 B1 | 2/2003 | Sesic |
| 6,755,862 B2 | 6/2004 | Keynan |
| 2003/0065329 A1 | 4/2003 | Vaughan |
| 2004/0254578 A1 | 12/2004 | Vaughan |
| 2006/0025773 A1 | 2/2006 | Yevmenenko |
| 2006/0111717 A1 | 5/2006 | Saueressig |
| 2006/0206044 A1* | 9/2006 | Simon ................ A61B 17/7225 602/23 |
| 2007/0100342 A1 | 5/2007 | Green |
| 2007/0173954 A1 | 7/2007 | Lavi |
| 2009/0062797 A1 | 3/2009 | Huebner |
| 2009/0187220 A1 | 7/2009 | Hamada |
| 2009/0259261 A1 | 10/2009 | Reiley |
| 2009/0306666 A1 | 12/2009 | Czartoski |
| 2010/0256638 A1 | 10/2010 | Tyber |
| 2011/0166609 A1 | 7/2011 | Duggal |
| 2013/0046311 A1 | 2/2013 | Blake |

OTHER PUBLICATIONS

International Preliminary Report on Patentability of the International Searching Authority for PCT/US2013/026397, dated Aug. 19, 2014, 6 pages.

* cited by examiner

CHARCO-RESIS IMPLANT, ALIGNMENT INSTRUMENT, SYSTEM AND METHOD OF USE

CROSS-REFERENCE TO RELATED APPLICATION

This application is a continuation of U.S. application Ser. No. 14/379,361 filed Aug. 18, 2014 and entitled Charco-Resis Implant, Alignment Instrument, System and Method of Use, which will issue as U.S. Pat. No. 10,524,845 on Jan. 7, 2020, which is a National Stage application based on International Application No. PCT/US2013/026397 filed Feb. 15, 2013, and published as WO 2013/123366 on Aug. 22, 2013 and entitled Charco-Resis Implant, Alignment Instrument, System and Method of Use, which claims priority benefit under 35 U.S.C. § 119(e) of U.S. provisional application No. 61/599,604 filed Feb. 16, 2012 and entitled Orthopedic Implant for correction and stabilization of the foot and/or ankle, which are incorporated herein by reference in their entireties.

FIELD OF THE INVENTION

The present invention relates generally to correction of a flat foot or rocker-bottom deformity, such as Charcot foot. More specifically, but not exclusively, the present invention concerns bone and elongate member implants and alignment guides for inserting the implants to correct a flat foot or rocker-bottom deformity.

SUMMARY OF THE INVENTION

Aspects of the present invention provide elongate member implants, bone implants, an alignment guide for inserting the elongate member and bone implants, and method for correcting a flat foot or rocker-bottom deformity.

In one aspect, provided herein is an implant system including a bone implant and an elongate member. The bone implant includes a proximal end, a distal end, a hole along a longitudinal axis, and at least one opening intersecting the hole. The elongate member includes a first end with a head portion, a second end with a coupling mechanism, and an opening along a longitudinal axis. The coupling mechanism of the elongate member engages the at least one opening to couple the bone implant to the elongate member.

In another aspect, provided herein is a bone fusion system. The system may include an implantable device, a rod, and an alignment guide. The implantable device includes a proximal end, a distal end, a longitudinal opening, and at least one hole extending into the longitudinal opening. The rod includes a first end with a head portion, a second end with an engagement member, and a hole extending along a longitudinal axis. An alignment guide including a first end and a second end, the first end of the alignment guide is configured to engage the proximal end of the implantable device and the second end of the alignment guide is configured to insert the rod into the patient's bones to engage the implantable device.

In yet another aspect, provided herein is a surgical method for fixing a patient's joint including selecting a fixation implant and a compression shaft. The method also includes determining a trajectory for the compression shaft and inserting the fixation implant into the patient's joint. The method may further include assembling an alignment guide. The alignment guide may include a drive tube, a driver, an alignment body, a sleeve, a first guide, and a second guide. The drive tube may include a longitudinal hole and may couple to the fixation implant at one end. The driver may be inserted into the longitudinal hole of the drive tube and may also couple to the proximal end of the fixation implant. The alignment body includes a first end, a second end, and a carriage. The carriage is configured to slidingly engage the first end of the alignment body and the second end of the alignment body engages the driver and may couple to the drive tube. The sleeve includes a longitudinal opening and may mate with the alignment body. The first guide includes a longitudinal hole and the first guide may be configured to engage the longitudinal opening in the sleeve. The second guide includes a longitudinal hole and is configured to engage the longitudinal hole of the first guide. The method may also include positioning the carriage and the sleeve relative to the fixation implant. The method may further include securing the carriage to the alignment body to maintain the sleeve position. The method may also include inserting a first guide and a second guide into the sleeve. The method also may include inserting a guide pin through the second guide and the patient's joint to intersect the fixation implant. The method may also include removing the second guide from the sleeve and inserting a drill over the guide pin to ream an opening in the patient's joint. The method may further include removing the drill and first guide from the sleeve. In addition, the method may include inserting the compression shaft over the guide pin, through the sleeve, and into the patient's joint. The method may further include removing the guide pin and inserting the compression shaft into the patient's joint. In addition, the method may include disassembling the alignment guide.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention.

DETAILED DESCRIPTION FOR CARRYING OUT THE INVENTION

Figure 1:
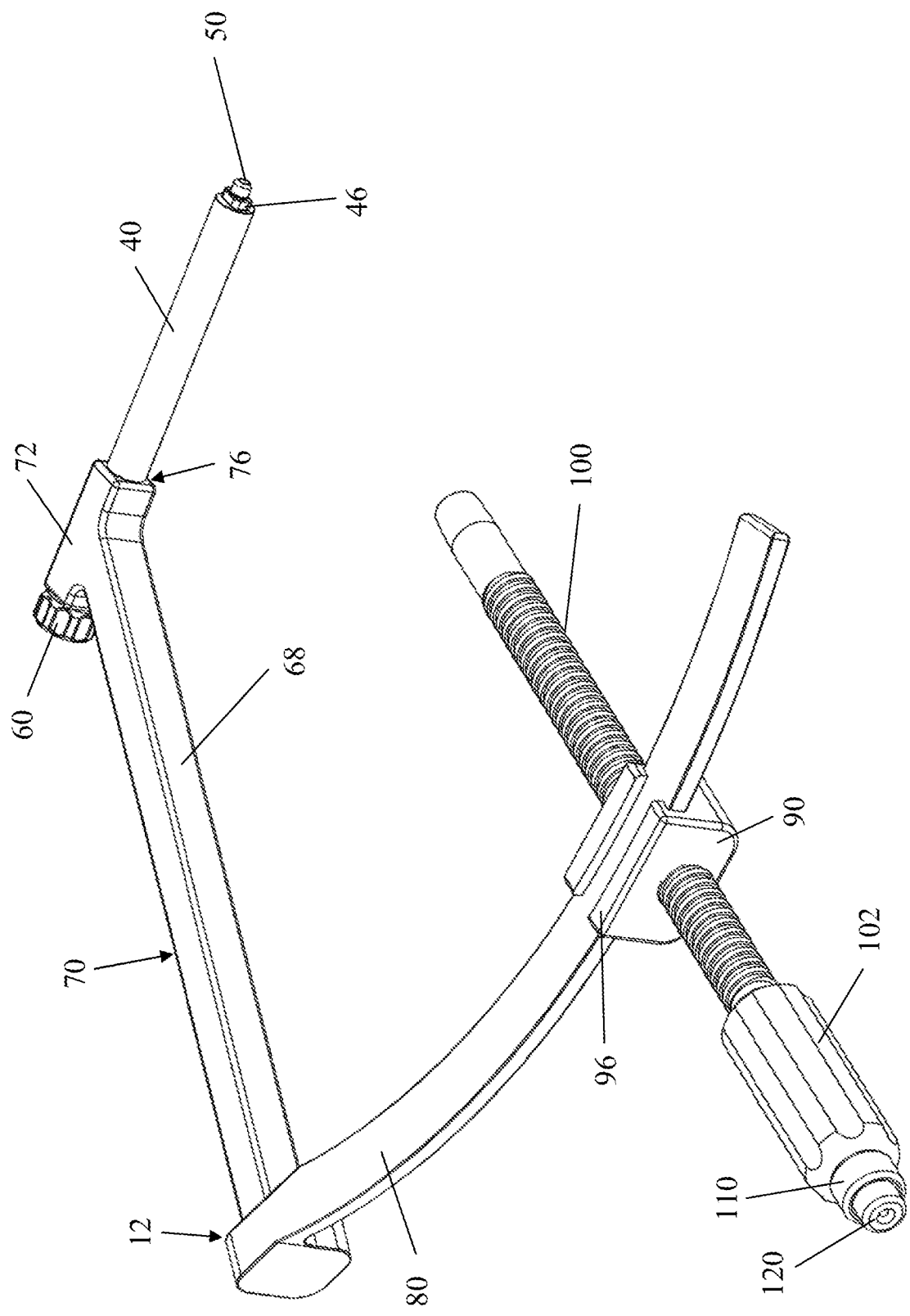
FIG. 1 is a top perspective view of an alignment guide, in accordance with an aspect of the present invention.

Generally stated, disclosed herein is an alignment guide for inserting an elongate member relative to a bone implant. A number of embodiments of bone implants are disclosed herein, as well as several embodiments of the elongate member. The terms "bone implant," "subtalar implant," "implantable device" and "fixation implant" may be used interchangeably as they essentially describe the same type of device. In addition, the terms "elongate member," "compression beam," "rod," and "compression shaft" may be used interchangeably as they essentially describe the same type of device. Further, a surgical method for implanting an implant including the subtalar implant and compression beam using the alignment guide is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure when referencing the implants, the term "proximal" will mean the portion of the implant closest or nearest the alignment guide. The term "distal" shall mean the portion of the implant farthest away from the alignment guide.

Referring to the drawings, wherein like reference numerals are used to indicate like or analogous components throughout the several views, and with particular reference to FIGS. 1-4, there is illustrated an exemplary embodiment alignment guide 10 for aligning a compression beam 130 with a subtalar implant 20. The alignment guide 10 may include an alignment body 12, a drive tube 40, a driver 50, a knob 60, a sleeve 100, a first guide 110, and a second guide 120. The alignment body 12 may include a support arm 70, an alignment arm 80, and a carriage 90. The driver 50 may couple to the knob 60 on a first end and engage the drive tube 40 on a second end. A first end of the support arm 70 may engage the driver 50 between the knob 60 and drive tube 40. The drive tube 40 may also couple to the support arm 70 on a first end and a subtalar implant 20 on a second end (See FIGS. 2 and 3). The support arm 70 may also couple with the alignment arm 80 on a second end. The carriage 90 may slidingly couple to the alignment arm 80 and the sleeve 100 may engage the carriage 90 relatively perpendicular to the alignment arm 80. The carriage 90 aligns the sleeve 100 into a desired position for inserting the compression beam 130 to engage the implanted subtalar implant 20 (See FIGS. 2 and 3). The second guide 120 may engage the sleeve 100 or the first guide 110 and the first guide 110 may engage the sleeve 100.

Figure 4:
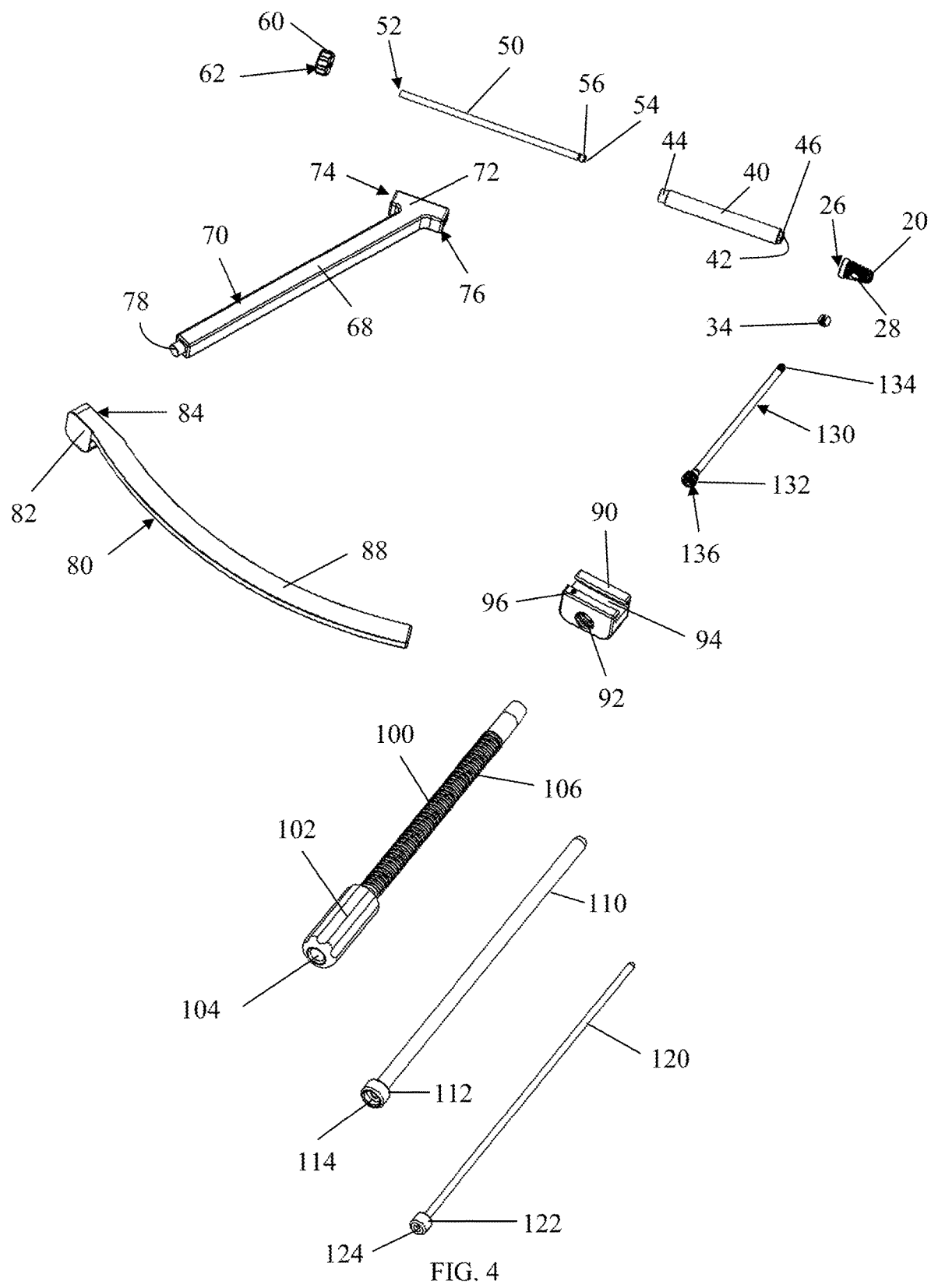
FIG. 4 is an exploded view of the alignment guide, bone implant, and elongate member of FIG. 2, in accordance with an aspect of the present invention.
Figure 5:
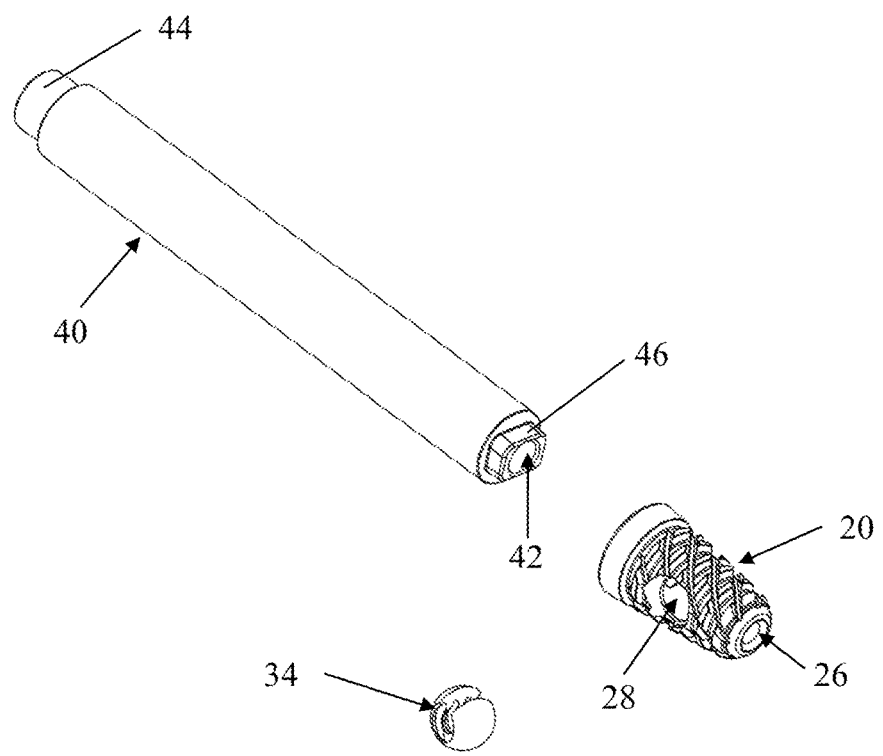
FIG. 5 is an exploded distal end view of the drive tube, bone implant, and split bushing of FIG. 4, in accordance with an aspect of the present invention.
Figure 6:
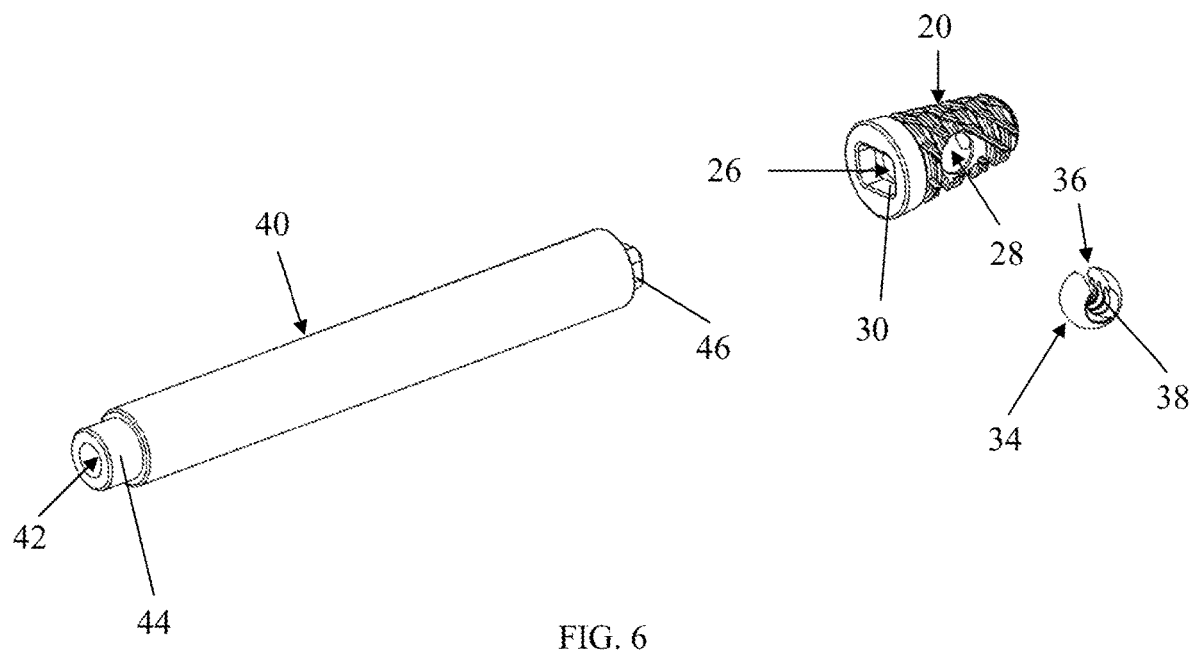
FIG. 6 is an exploded proximal end view of the drive tube, bone implant, and split bushing of FIG. 4, in accordance with an aspect of the present invention.
Figure 15:
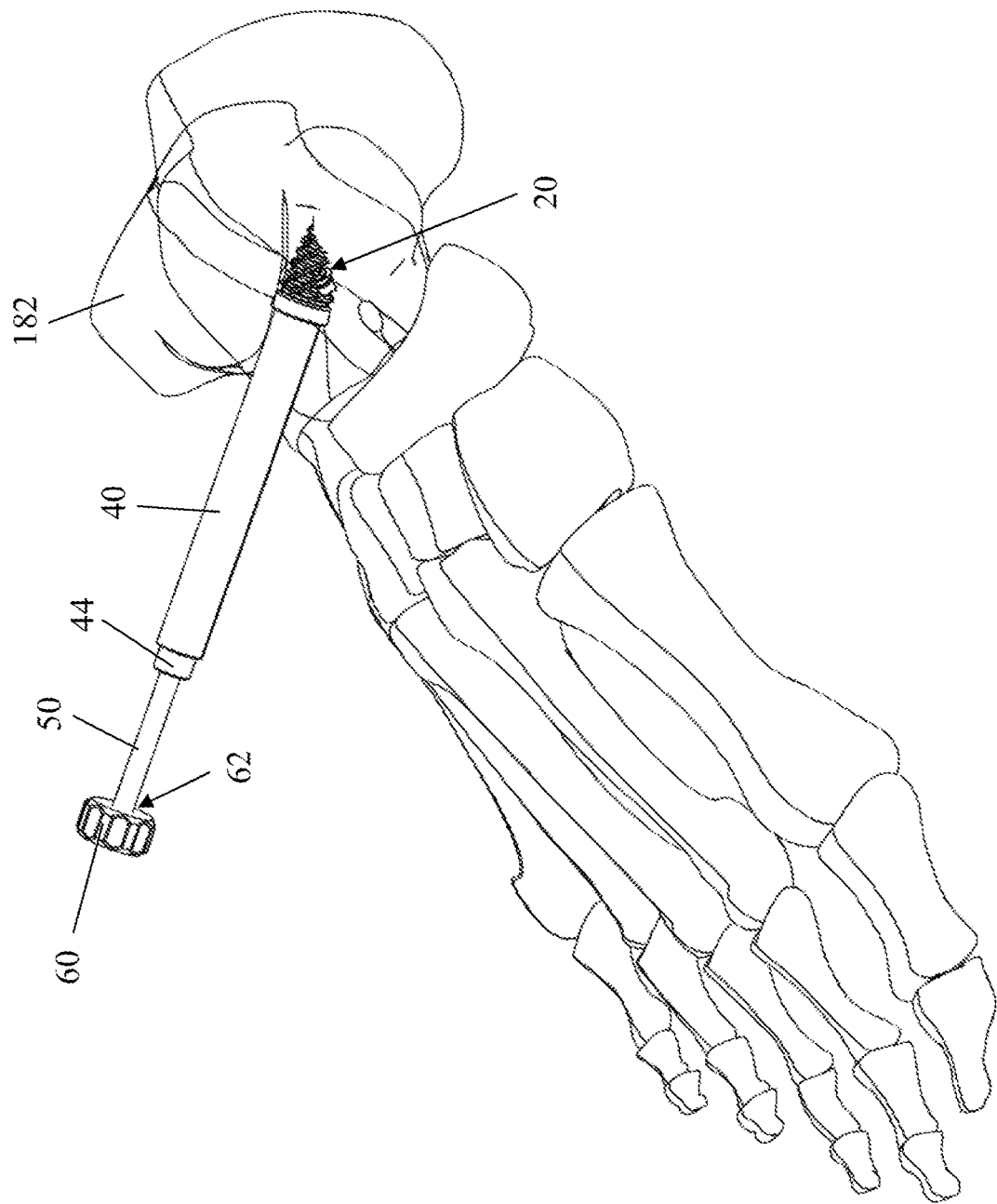
FIG. 15 is a perspective view of the bone implant of FIG. 10 engaging the drive tube and driver of the alignment guide of FIG. 1 while being inserted into a patient's foot, in accordance with an aspect of the present invention.

As shown in the exploded views of FIGS. 4-6, the drive tube 40 may include a through hole 42 along the longitudinal axis of the drive tube 40. The drive tube 40 may also include a coupling protrusion 44 on a first end and an implant engagement protrusion 46 on a second end opposite the first end. The implant engagement protrusion 46 of the drive tube 40 may engage the engagement cavity 30, seen in FIGS. 6-10, of the subtalar implant 20. The implant engagement protrusion 46 and the engagement cavity 30 may have corresponding shapes, which may have, for example, polygonal or multi-lobed shapes. The coupling protrusion 44 may be configured to couple the drive tube 40 to an engagement opening 76 of the support arm 70. The driver 50 may pass through the hole 42 of the drive tube 40 to engage the longitudinal through hole 26 of the subtalar implant 20. The driver 50 may include a longitudinal opening 52 and an engagement end 54 at the inferior end of the driver 50 for mating with a subtalar implant 20. The engagement end 54 may also include a channel 56. The proximal end of the driver 50 may couple with the engagement opening 62 of the knob 60 for insertion of the subtalar implant 20 into a patient, as seen in FIG. 15.

Figure 2:
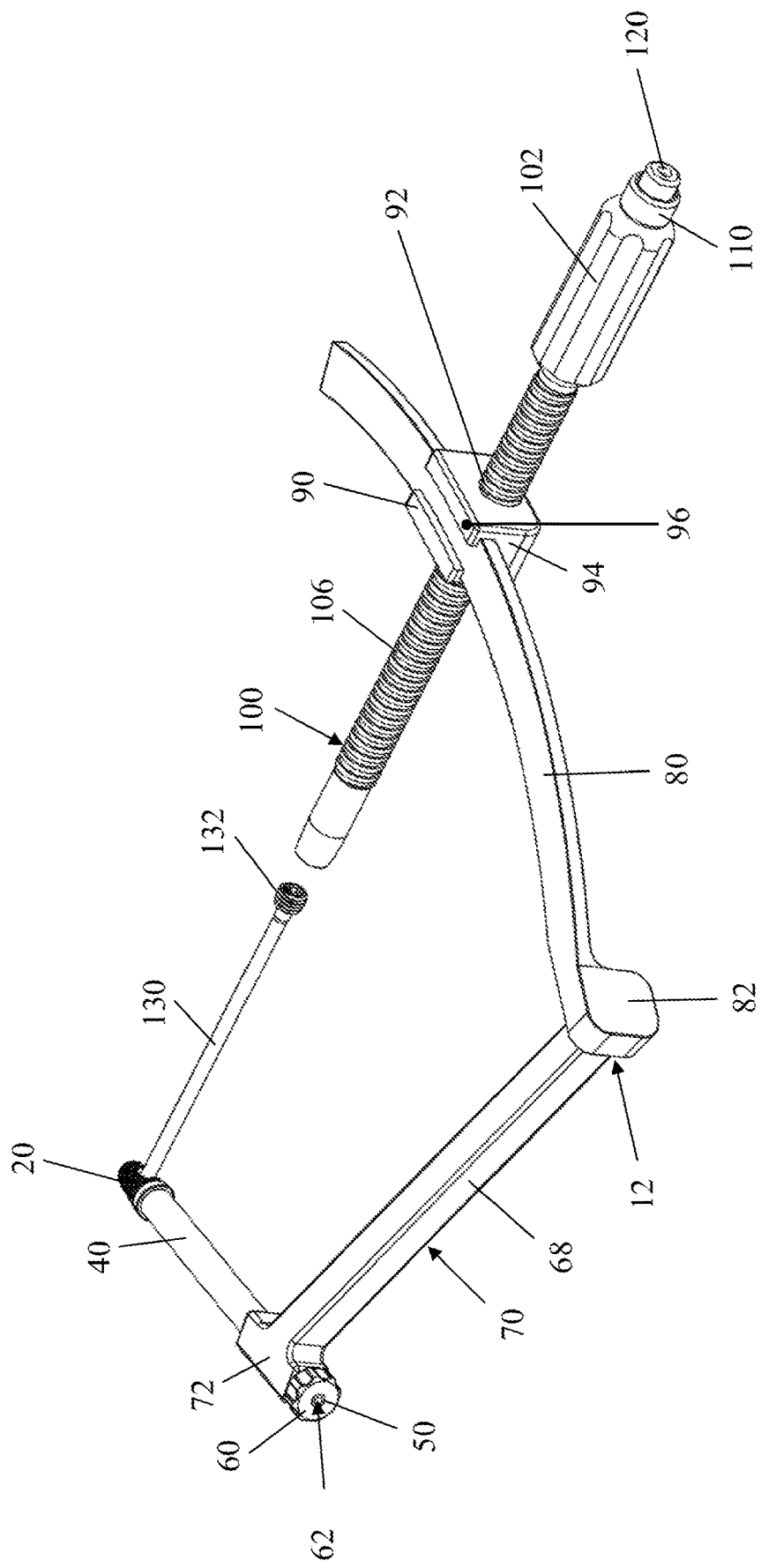
FIG. 2 is a top perspective view of the alignment guide of FIG. 1 attached to a bone implant and an elongate member, in accordance with an aspect of the present invention.

After insertion of the subtalar implant 20 into a patient, as shown in FIGS. 1-3 and 16, the driver 50 may be engage the support arm 70. As shown in FIG. 4, the support arm 70 may include a base 68 with a first end and a second end. The first end of the base 68 includes an alignment end 72 with a through hole 74 and an engagement opening 76, as seen in FIG. 4. The second end of the base 68 includes an engagement protrusion 78, shown in FIG. 4. The driver 50 may be inserted into the through hole 74 of the support arm 70 by removing the knob 60, sliding the support arm 70 onto the driver 50 and reattaching the knob 60. As seen in FIGS. 1 and 4, the support arm 70 is slid onto the driver 50, the engagement opening 76 of the alignment end 72 engages the coupling protrusion 44 of the drive tube 40. The support arm 70 may couple with the alignment arm 80 on the second end of the base 68, as shown in FIGS. 1 and 2.

Figure 3:
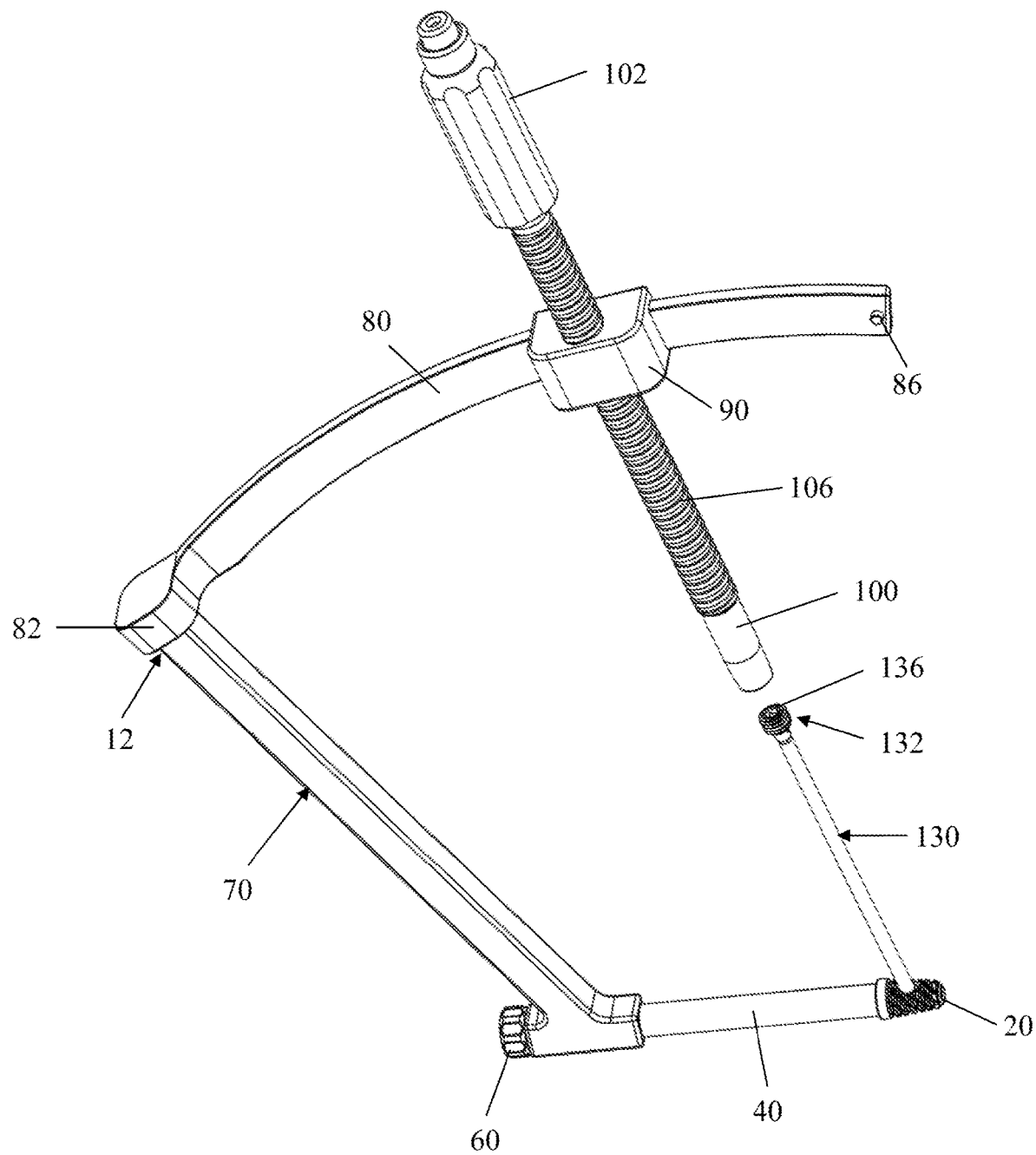
FIG. 3 is a bottom perspective view of the alignment guide, bone implant, and elongate member of FIG. 2, in accordance with an aspect of the present invention.

As shown in FIGS. 3 and 4, the alignment arm 80 may include an engagement end 82 with an engagement opening 84 on a first end and a stop protrusion 86 on the second end. The first end and the second end of the alignment arm 80 may be connected by an arm member 88. The support arm 70 may couple with the alignment arm 80 by inserting the engagement protrusion 78 of the support arm 70 into the engagement opening 84 of the alignment arm 80.

As seen in FIG. 1, the carriage 90 may engage the arm member 88 of the alignment arm 80. The carriage 90 may include a threaded through hole 92 and an engagement channel 94, as shown in FIG. 4. The engagement channel 94 may be, for example, perpendicular to the through hole 92. Opposite the engagement end 82 of the alignment arm 80, the engagement channel 94 of the carriage 90 may be inserted onto the arm member 88 to slide along the alignment arm 80. The arm member 88 may include a stop protrusion 86, shown in FIG. 3, to prevent the carriage 90 from sliding off the end of the arm member 88 once attached to the alignment arm 80. The channel 94 of the carriage 90 may move along the arm member 88 of the alignment arm 80 to allow for alignment of the compression beam 130 with the already implanted subtalar implant 20. Once a desired trajectory is obtained, a locking mechanism 96 (See FIGS. 1-2 and 4) may be used to secure the carriage 90 to the arm member 88. The locking mechanism 96 may be, for example, a set screw.

Figure 18:
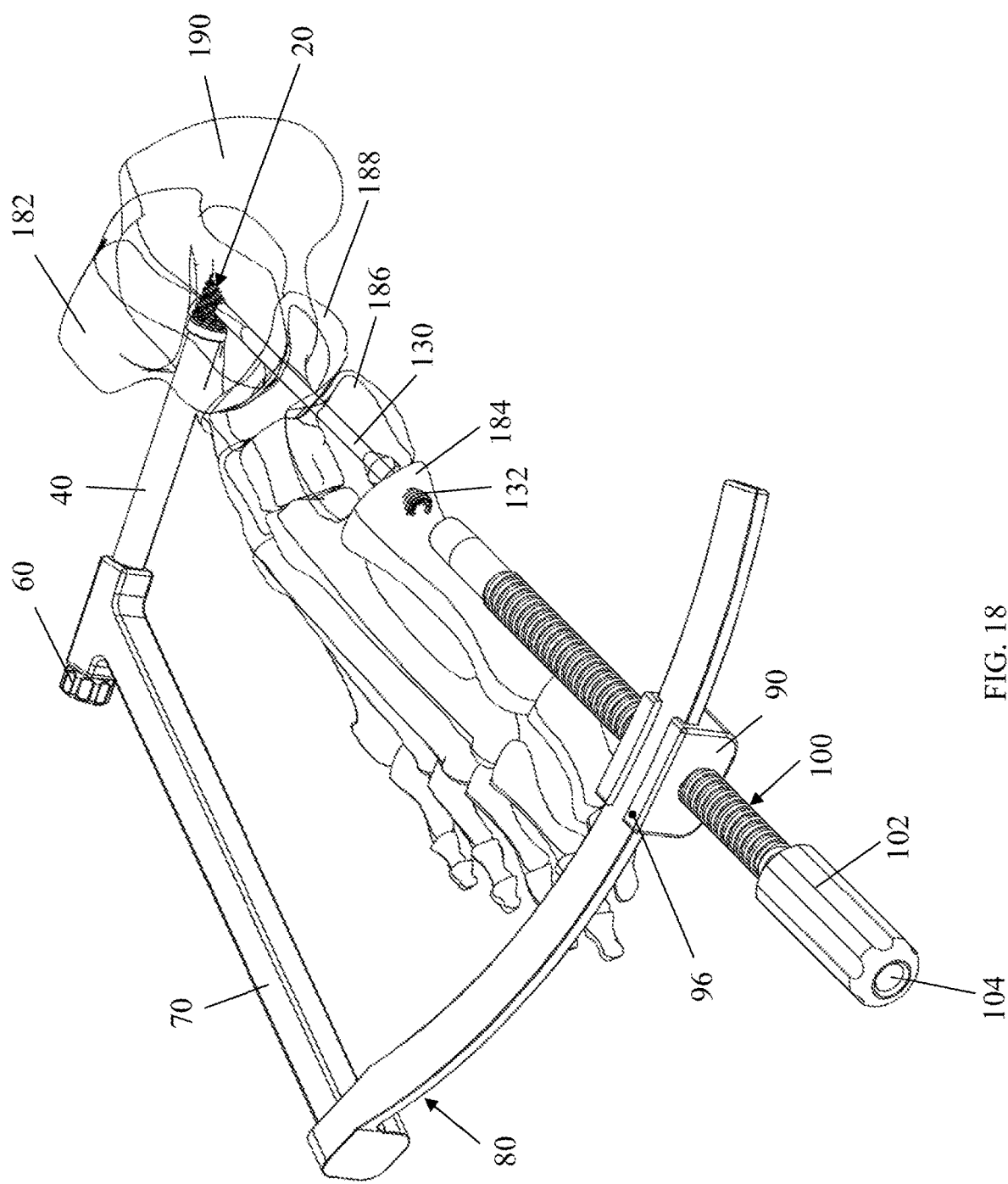
FIG. 18 is a perspective view of the alignment guide of FIG. 1 configured to insert the elongate member of FIG. 13 and engaging the bone implant of FIG. 10, in accordance with an aspect of the present invention.

As shown in FIGS. 2-3 and 18, the compression beam 130 may be aligned with the subtalar implant 20 by inserting the sleeve 100 into the threaded through hole 92 of the carriage 90. The sleeve 100 may include an adjustment knob 102 for inserting the sleeve 100 into the threaded hole 92 of the carriage 90 and to adjust the position of the sleeve 100 relative to the subtalar implant 20. The terms "screw sleeve" and "sleeve" may be used interchangeably as they essentially refer to the same device. The screw sleeve 100 may also include threads 106 longitudinally along the exterior of the screw sleeve 100 below the adjustment knob 102 for mating with the threaded hole 92 of the carriage 90. In addition, the screw sleeve 100 may include a longitudinal opening 104 (See FIG. 4) through the screw sleeve 100. The longitudinal opening 104 of the screw sleeve 100 may be configured for insertion of a first guide 110 and/or a second guide 120.

The second guide 120, as shown in FIG. 4, may include a head 122 for engaging the adjustment knob 102 of the screw sleeve 100 or a head 112 of the first guide 110. The second guide 120 may also include a longitudinal through hole 124 for insertion of a guide pin (not shown) into the patient's bones. The second guide 120 may be, for example, a k-wire guide. The guide pin may be, for example, a temporary fixation pin, a k-wire, or the like. The first guide 110, as shown in FIG. 4, may include a head 112 and a longitudinal through hole 114. The first guide 110 may be, for example, a drill guide. The second guide 120 may be inserted into the opening 104 of the screw sleeve 100 or into the through hole 114 of the first guide 110 to align the second guide 120 relative to the subtalar implant 20. The longitudinal opening 114 of the first guide 110 may also be used for insertion of a drill (not shown), which may be used to drill over the guide pin for insertion of the compression beam 130 into the patient's bones. The opening 104 of the screw sleeve 100 may also allow for insertion of the compression beam 130 attached to an insertion tool (not shown) for correct alignment with the subtalar implant 20.

Figure 12:
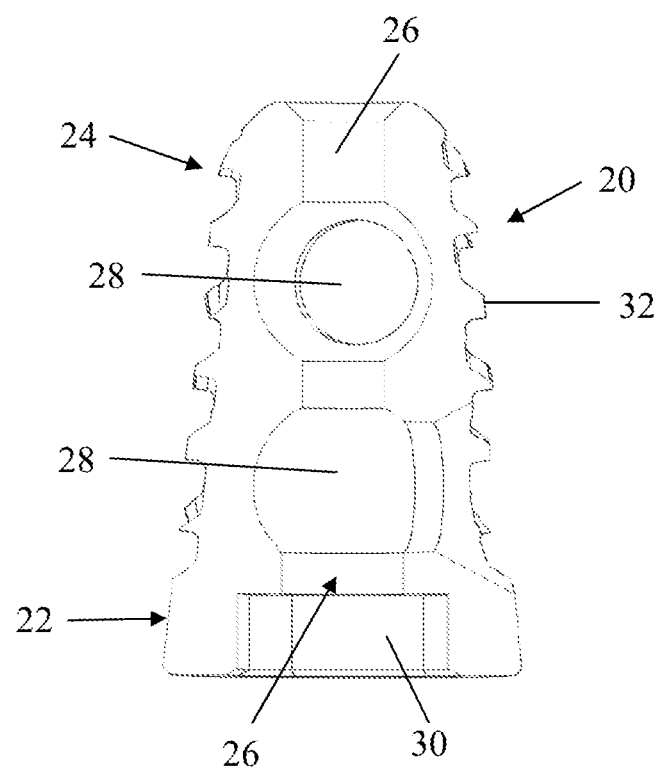
FIG. 12 is a cross-sectional view of the bone implant of FIG. 11 as viewed along line 12-12 in FIG. 11, in accordance with an aspect of the present invention.

Referring now to FIGS. 7-10, a plurality of subtalar implants 20 are shown. The subtalar implants 20 may include a proximal end 22 and a distal end 24. The subtalar implants 20 may also be, for example, tapered from the proximal end 22 to the distal end 24 creating, for example, a bullet or cone shape, as shown in FIG. 12. The subtalar implants 20 may also include a longitudinal hole or opening 26 from the proximal end 22 to the distal end 24. The longitudinal hole or opening 26 may be, for example, a through hole. The terms "longitudinal hole," "longitudinal opening" and "through hole" may be used interchangeably as they essentially refer to the same structure. Alternatively, the subtalar implant 20 may include a longitudinal hole 26 extending into the subtalar implant 20 from the proximal end 22, which does not extend all the way to the distal end 24. In addition, the subtalar implants 20 may include at least one opening 28 relatively perpendicular to and intersecting with the hole 26, as seen in FIG. 12. The at least one opening 28 may be, for example, a blind hole. The at least one opening 28 of the subtalar implants 20 may be, for example, one opening along the longitudinal axis of the subtalar implants 20, two openings spaced apart along the longitudinal axis of the subtalar implants 20 and positioned approximately 90 degrees or 180 degrees from each other, or three openings spaced apart along the longitudinal axis of the subtalar implants 20 and positioned approximately 120 degrees apart from each other. The subtalar implants 20 may also include an engagement cavity 30 at the proximal end 22 of the opening 26 for connecting with a driver 50 and drive tube 40 for insertion into a patient's bones. The subtalar implants 20 may have at least one bushing 34 (See FIG. 4) in the at least one opening 28 for engaging the compression beam 130. The bushing 34 (See FIG. 10) may include a cavity 36 with threads 38 for engaging the threaded tip 142 (See FIGS. 13-14) of the compression beam 130. Alternatively, the at least one opening 28 may be threaded to engage the compression beam 130.

Figure 7:
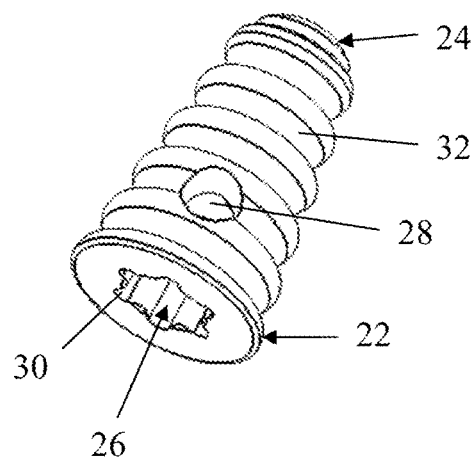
FIG. 7 is a perspective view of the bone implant of FIG. 2, in accordance with an aspect of the present invention.
Figure 8:
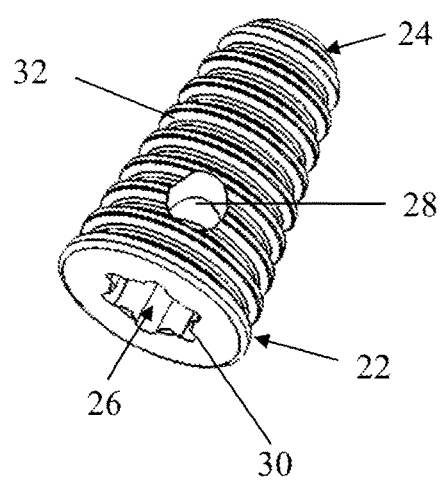
FIG. 8 is a perspective view of another embodiment of the bone implant, in accordance with an aspect of the present invention.
Figure 9:
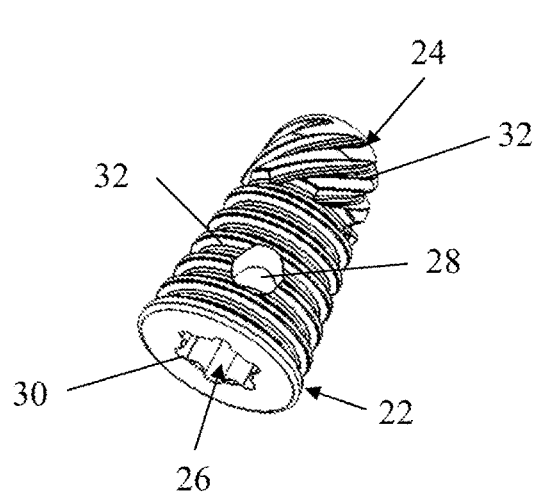
FIG. 9 is a perspective view of yet another embodiment of the bone implant, in accordance with an aspect of the present invention.
Figure 10:
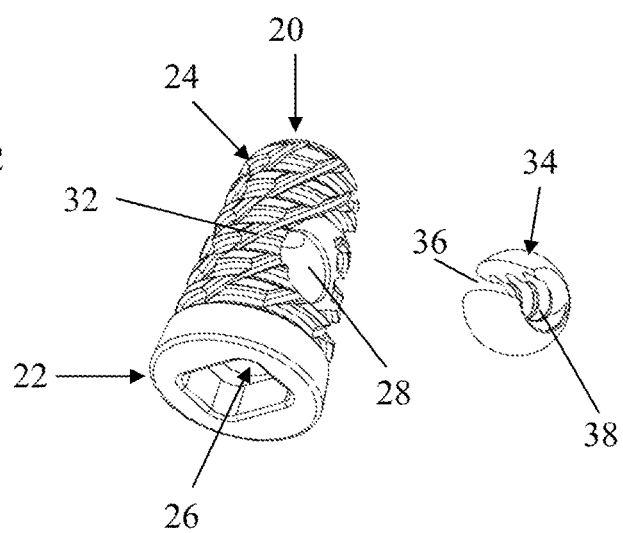
FIG. 10 is an exploded perspective view of a further embodiment of the bone implant and a bushing, in accordance with an aspect of the present invention.
Figure 11:
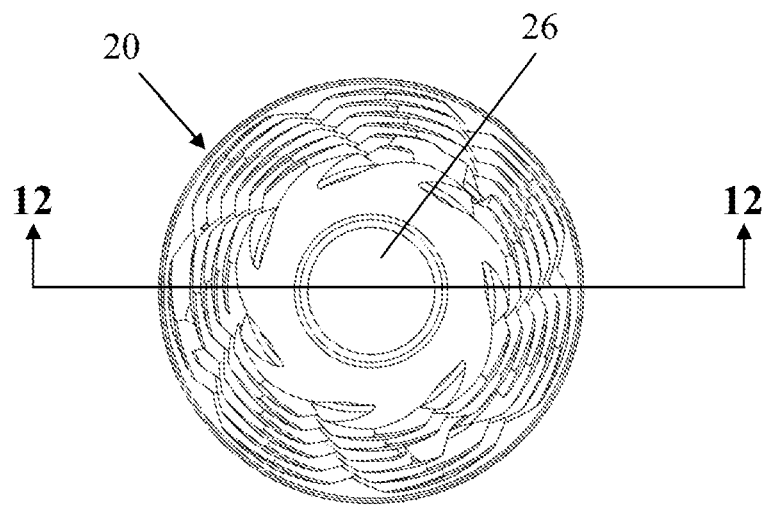
FIG. 11 is a top view of the bone implant of FIG. 10, in accordance with an aspect of the present invention.

The subtalar implants 20 may also include a plurality of grooves 32 which may be in various arrangements. Examples of these grooves 32 are shown in FIGS. 6-10. The plurality of grooves 32 may extend, for example, horizontally around the circumference of the implants 20, at an angle around the circumference of the implants 20, and both horizontally and at an angle around the circumference of the implants 20. The plurality of grooves 32 may be horizontal relative to the longitudinal axis of the implants 20, such that, the grooves 32 are substantially perpendicular to the longitudinal axis as they extend around the circumference of the implants 20. The plurality of grooves 32 may include, for example, sharp edges, rounded edges or a combination of both sharp and rounded edges. In addition, the size and depths of the plurality of grooves 32 and the spacing (or pitch) between each groove of the plurality of grooves 32 may vary on the implants 20. For example, as illustrated, FIGS. 7 and 8 show the plurality of grooves 32 extending horizontally around the circumference of the implants 20 relative to the longitudinal axis of the implants 20, however the plurality of grooves 32 shown in FIG. 7 are larger and spaced farther apart than the plurality of grooves 32 shown in FIG. 8. The plurality of grooves 32 may, for example, extend horizontally around the circumference of the implant 20 relative to the longitudinal axis of the implant 20 on a first portion and extend at an angle around the circumference of the implant 20 on a second portion, as shown in FIG. 9, the proximal end 22 of the implant 20 includes the horizontal grooves 32 and the distal end 24 of the implant 20 includes the angled grooves 32, although other arrangements of the plurality of grooves 32 are also contemplated. As shown in FIG. 10, the plurality of grooves 32 may, for example, extend both horizontally relative to the longitudinal axis and at an angle from the proximal end 22 to the distal end 24 in an overlapping pattern relative to each other. As shown in FIG. 10, the first portion and second portion of the implant 20 may overlap relative to each other.

Figure 13:
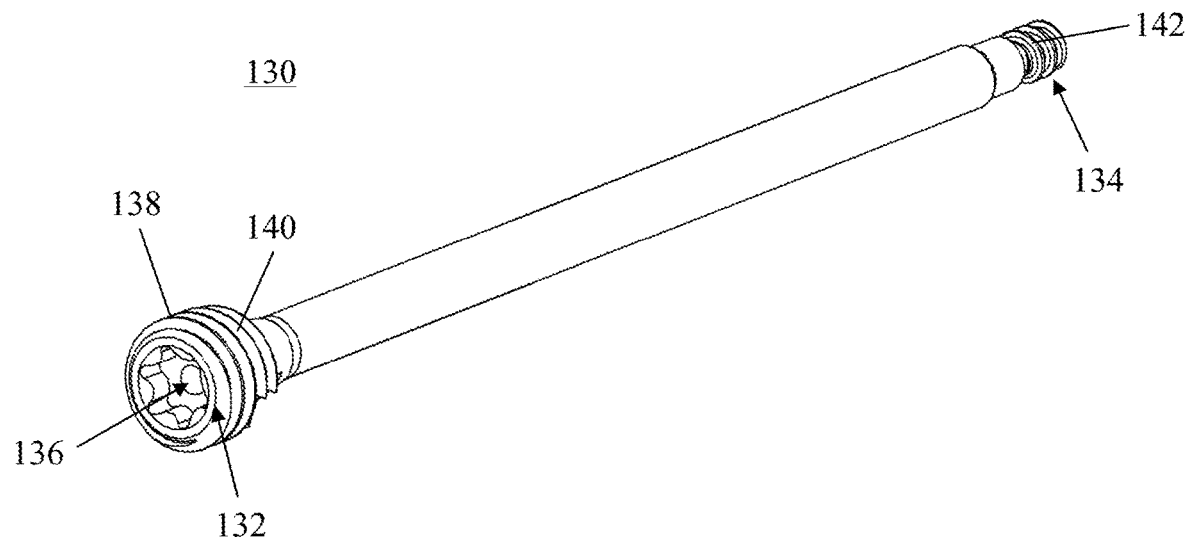
FIG. 13 is a perspective view of the elongate member of FIG. 2, in accordance with an aspect of the present invention.
Figure 14:
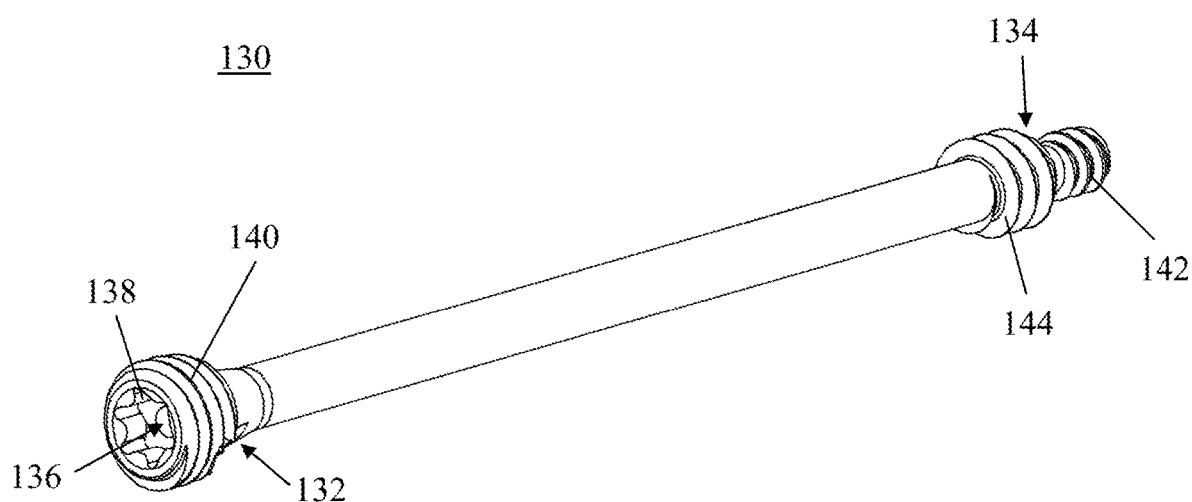
FIG. 14 is a perspective view of another embodiment of the compression screw, in accordance with an aspect of the present invention.

Referring now to FIGS. 13 and 14, two embodiments of the compression beam 130 are shown. The compression beam 130 may include a first end 132, a second end 134, and a through hole 136 extending longitudinally from the first end 132 to the second end 134. The terms "through hole," "longitudinal hole," and "longitudinal opening" may be used interchangeably as they essentially refer to the same structure. Alternatively, the hole 136 may not be a through hole, rather the hole 136 may extend into the compression beam 130 from the first end 132 but not extend all the way through to the second end 134. The first end 132 of the compression beam 130 may include a head portion with an engagement opening 138 for engaging an insertion tool (not shown) and a coupling mechanism 140 including fixation threads for engagement with the patient's bone. The second end 134 of the compression beam 130 may include a threaded tip 142 for engaging the at least one bushing 34 of the subtalar implant 20. The terms "second end," "threaded tip," "coupling mechanism" and "engagement member" may be used interchangeably as they essentially describe the same type of component. Alternatively, if the subtalar implant 20 does not include bushings 34, the threaded tip 142 may be inserted directly into the at least one opening 28 of the subtalar implant 20 to couple the compression beam 130 to the subtalar implant 20. The threaded tip 142 may be, for example, a machine thread. In an alternative embodiment, shown in FIG. 14, the second end 134 of the compression beam 130 may also include a compression engagement portion 144 adjacent to the threaded tip 142. The compression engagement portion 144 may have a larger diameter than the diameter of the threaded tip 142 for engaging the patient's bone. The compression engagement portion 144 may also assist with compression of the patient's bones during insertion of the compression beam 130. The compression beam 130 may be, for example, made of titanium, stainless steel, nitinol, or like metals. As depicted in FIGS. 13 and 14, the second end 134 is a threaded tip 142, although alternative second ends 134 which are not threaded are also contemplated, for example, taper press fits, snap rings, and the like.

Figure 16:
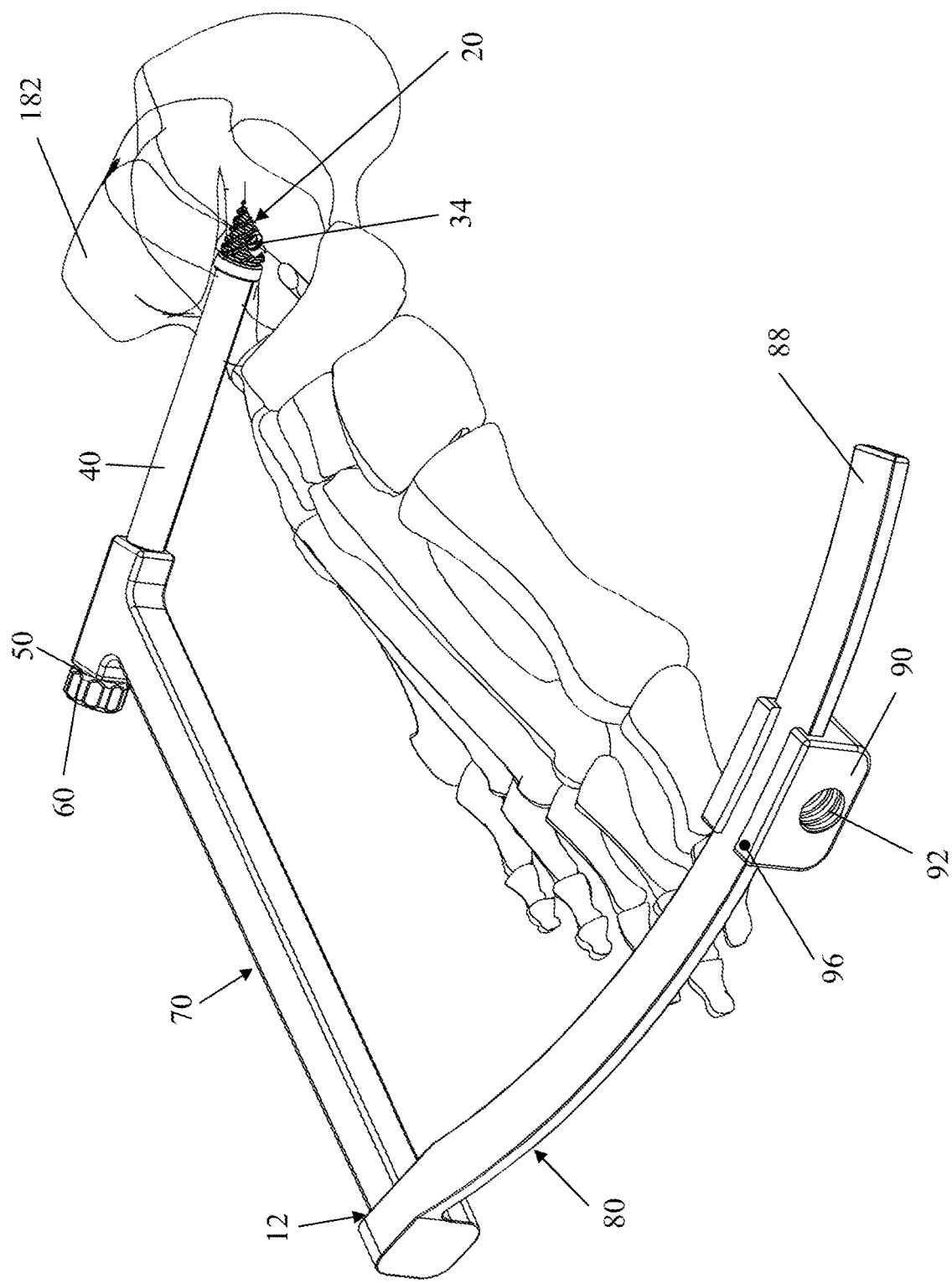
FIG. 16 is a perspective view of the alignment body of the alignment guide of FIG. 1 engaging the drive tube and driver of FIG. 15, in accordance with an aspect of the present invention.
Figure 20:
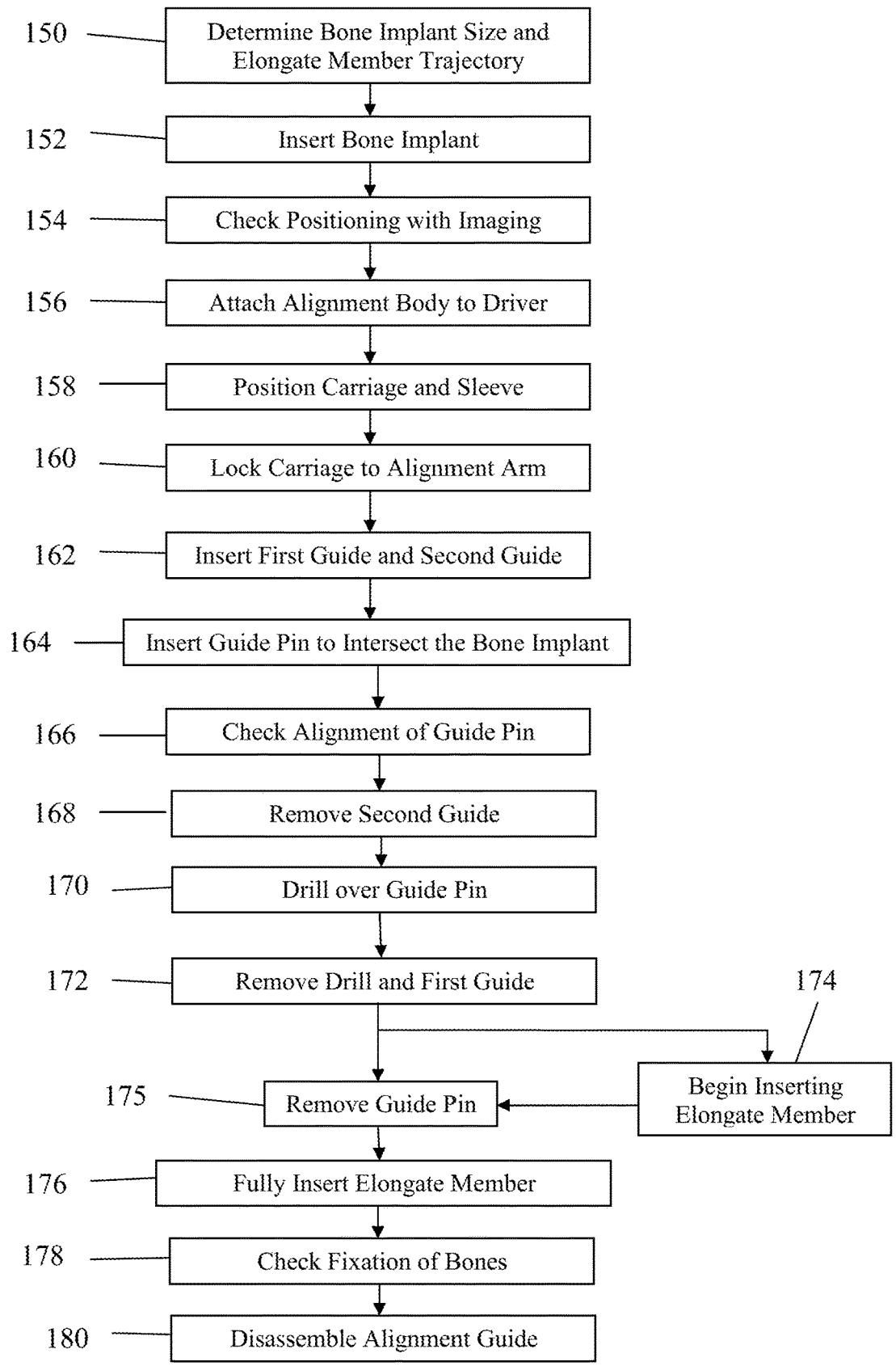
FIG. 20 depicts one embodiment of a surgical method for implanting the bone implant and elongate member into a patient's body, in accordance with an aspect of the present invention.

Referring now to FIG. 20, a surgical method for inserting an implant system that may include a subtalar implant 20 and compression beam 130 using the alignment guide 10 is shown. The surgical method may include the step 150 of using an x-ray template of the patient's joint to determine the size of the subtalar implant 20 and trajectory of the compression beam 130. The next step 152 may include inserting the subtalar implant 20 into the patient's hind foot, for example, within the joint space of the talus bone 182 and calcaneous bone 190. The drive tube 40 and driver 50 may be used to insert the subtalar implant 20 into the patient's hind foot at a set distance based on the x-ray template, as shown in FIG. 15. Next a physician may perform step 154 using an imaging technique, for example, fluoroscopy, of the patient's joint to check positioning of the subtalar implant 20. Once the desired positioning of the subtalar implant 20 is confirmed, the alignment body 12 may be attached in step 156, as shown in FIG. 16. The alignment body 12 may be attached by, for example, sliding the support arm 70 onto the driver 50 and coupling the support arm 70 to the drive tube 40. The knob 60 may be removed and replaced in order to slide the support arm 70 onto the driver 50. In addition, step 156 may include coupling the alignment arm 80 with a carriage 90 attached to the support arm 70, as seen in FIG. 16. Alternatively, the carriage 90 may be inserted onto the alignment arm 80 after coupling it to the support arm 70.

Figure 17:
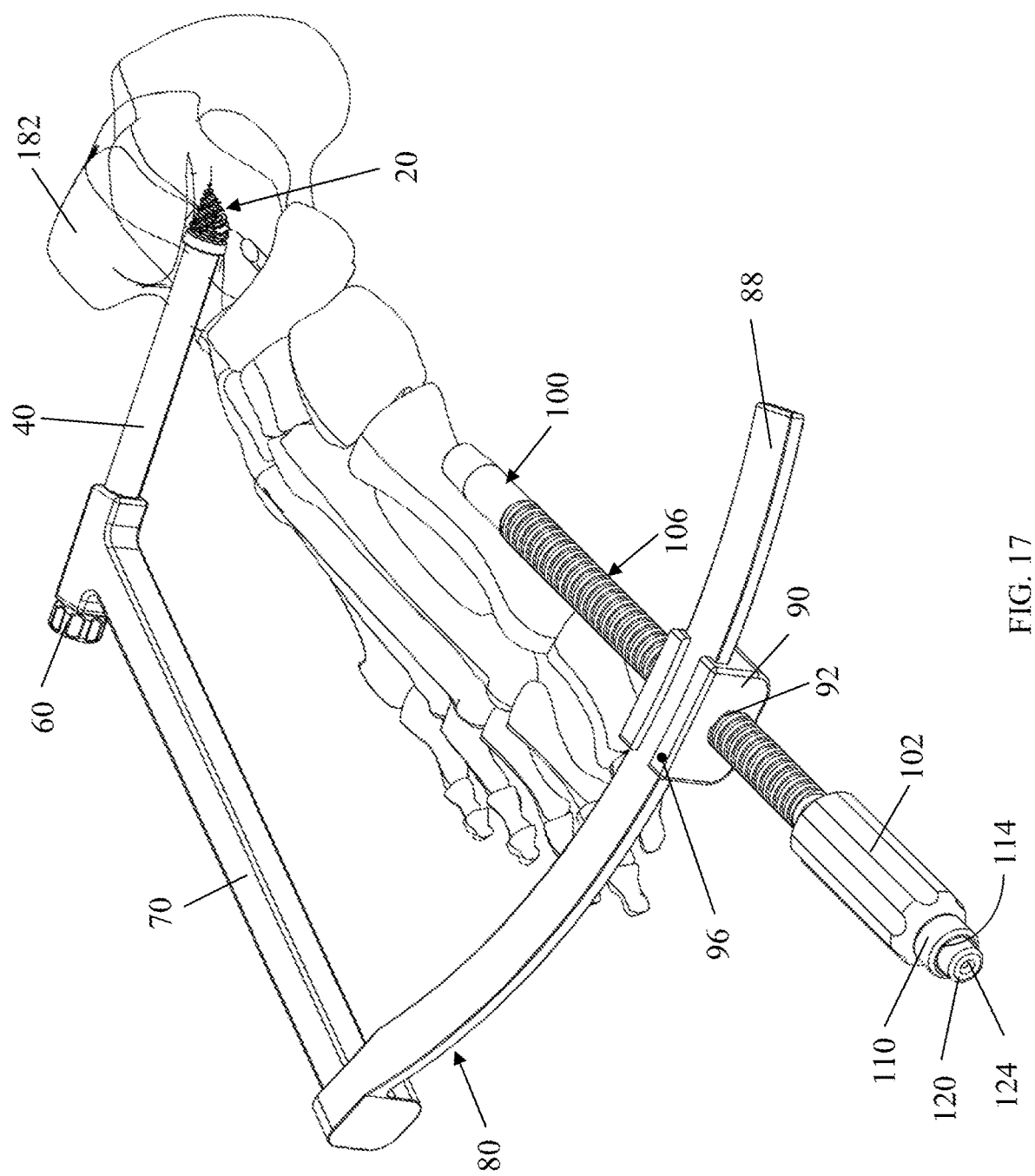
FIG. 17 is a perspective view of the alignment guide of FIG. 1 engaging the bone implant of FIG. 10 inserted into a patient's foot, in accordance with an aspect of the present invention.
Figure 19:
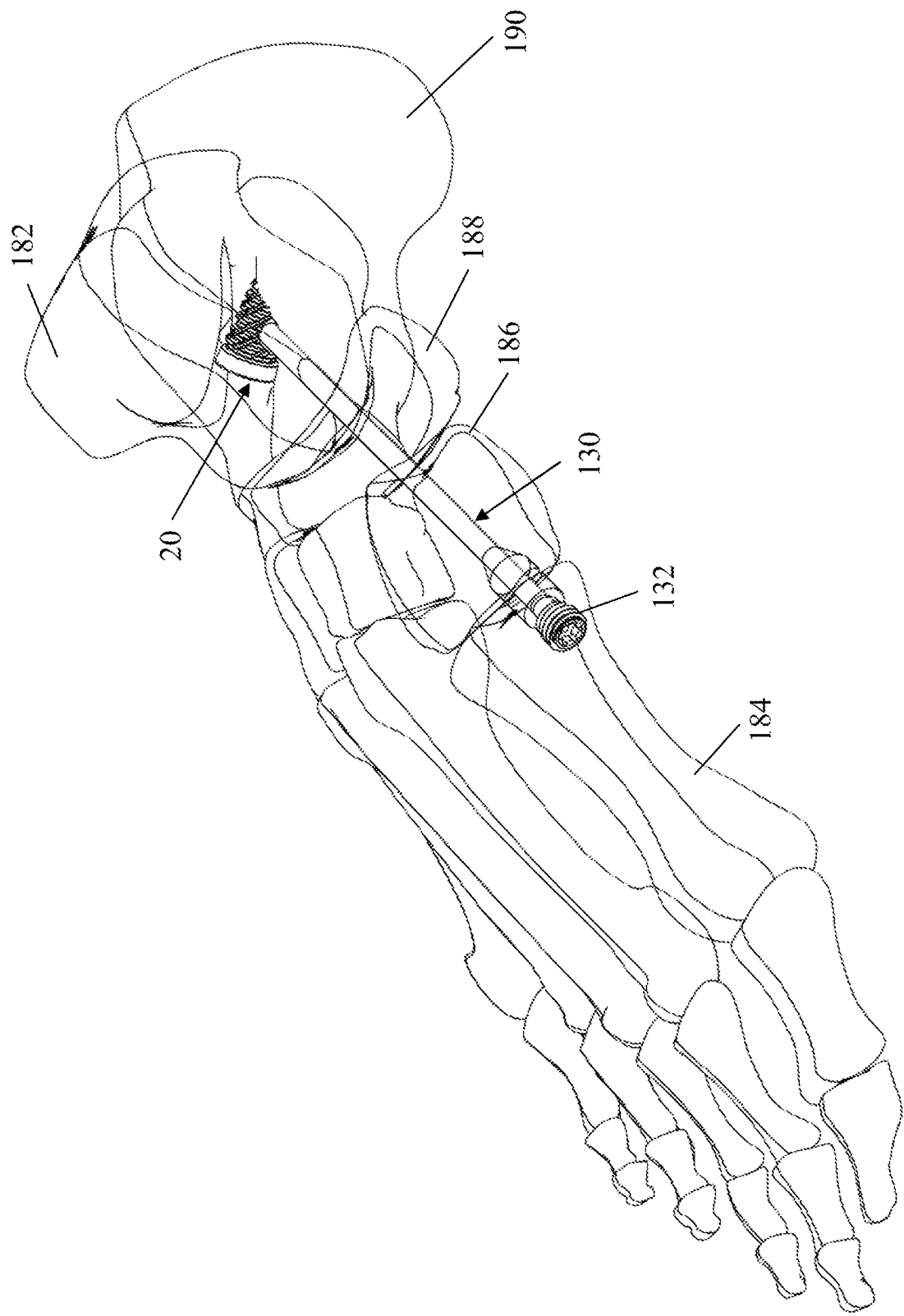
FIG. 19 is a perspective view of the bone implant of FIG. 10 and the elongate member of FIG. 13 implanted into a patient's foot, in accordance with an aspect of the present invention.

As seen in FIG. 17, in the next step 158, the carriage 90 may be positioned along the alignment arm 80 relative to the subtalar implant 20 to determine the trajectory of the compression beam 130. The screw sleeve 100 may be inserted into the threaded hole 92 in the carriage 90. Once a desired trajectory of the compression beam 130 is reached, step 160 may include locking the carriage 90 to the alignment arm 80 using a locking mechanism (not shown). The next step 162 may include inserting the first guide 110 into the opening 104 of the screw sleeve 100 and the second guide 120 into the opening 114 of the first guide 100, as shown in FIG. 17. Next a physician may insert a guide pin through the through hole 124 of the second guide 120 and through the patient's bones to intersect with the subtalar implant 20 in step 164. After insertion of the guide pin into the patient's bones, step 166 may include checking the alignment of the guide pin (not shown) using an imaging technique, for example, fluoroscopy. Once proper alignment of the guide pin is confirmed, if the second guide 120 has not already been removed, the second guide 120 may be removed in step 168. Next, in step 170, a drill (not shown) may be inserted into the opening 114 of the first guide 110 over the guide pin (not shown) and an opening drilled for insertion of the compression beam 130. As shown in FIG. 19, the opening may be drilled into the patient's bones, for example, the first metatarsal 184, the medial cuneiform 186, the navicular 188, and the talus 182 where it engages the subtalar implant 20. Step 172 may include removing the drill and first guide 110 from the opening 104 of the screw sleeve 100.

After the drill and first guide 110 are removed, as shown in FIG. 18, the compression beam 130 may be attached to a tool (not shown) and inserted over the guide pin and through the opening 104 of the screw sleeve 100 in step 174. Once the compression beam 130 passes through the screw sleeve 100 and begins engaging the drilled opening in the patient's bones, the guide pin may be removed in step 182. Alternatively, the guide pin may be removed prior to inserting the compression beam 130. As shown in FIG. 20, the alternative method may include removing the guide pin after the drill and first guide are removed, and then the compression beam may be inserted into the patient as discussed below with reference to step 176. Once the guide pin is removed, the compression beam 130 may be inserted through the patient's bones to engage the subtalar implant 20 in step 176, as shown in FIG. 18. Specifically, the threaded tip 142 of the compression beam 130 engages the at least one opening 28 of the subtalar implant 20 or a cavity 36 (See FIGS. 6 an 10) in the bushing 34 (See FIGS. 4, 6 and 10) that is positioned in the at least one opening 28 of the subtalar implant 20 to secure the compression beam 130 to the subtalar implant 20. The compression beam 130 is fully inserted into the patient's bones once it is within or flush with the bone. Next step 178 may include checking the fixation using at least one imaging technique, for example, fluoroscopy. After fixation is confirmed, the alignment guide 10 may be disconnected from the subtalar implant 20 and compression beam 130 in step 180. The implanted subtalar implant 20 and connected compression beam 130 are shown in FIG. 19 after final placement.

The above described method and alignment guide 10 may be used to insert the compression beam 130 through the base of the metatarsal to mate with the subtalar implant 20, as shown in FIGS. 15-19. Alternatively, the above described method and alignment guide 10 may be used to insert the compression beam 130 through the head of the metatarsal to mate with the subtalar implant 20. In an additional alternative embodiment, the above described method that uses the alignment guide 10 with an alternative alignment arm 80 may be used to insert the compression beam 130 through the lateral column of the patient's foot to mate with the subtalar implant 20.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A surgical method for fixing at least two portions of bone of a patient, comprising:
    selecting an implant and a shaft, wherein the implant has at least one of a cylindrical shape and a conical shape and wherein the implant has an exterior surface extending from a proximal end to a distal end of the implant;
    determining a trajectory for insertion of the shaft;
    inserting a drill along the trajectory into a joint space in the patient's hind foot to ream an opening into a portion of an articulating surface of a talus bone and an articulating surface of a calcaneus bone;
    inserting the implant into the joint space in the patient's hind foot between the articulating surface of the talus bone and the articulating surface of the calcaneus bone;
    inserting the drill into the at least two portions of bone along the trajectory to ream an opening in the at least two portions of bone, wherein the at least two portions of bone are selected from metatarsal bones and tarsal bones;
    removing the drill from the at least two portions of bone; and
    inserting the shaft across the at least two portions of bone along the trajectory, into the reamed opening and into the exterior surface of the implant positioned in the joint space of the patient's hind foot to couple the shaft to the implant such that the at least two portions of bone are fixed relative to each other.

2. The surgical method of claim 1, further comprising:
    assembling an alignment guide, wherein the alignment guide comprises:
        a driver that couples to the proximal end of the implant;
        an alignment body including a first end, a second end, and a carriage, the carriage is configured to slidingly engage the first end of the alignment body, the second end of the alignment body engages the driver;
        a sleeve including a longitudinal opening, the sleeve mating with the alignment body;
        a first guide including a longitudinal hole, the first guide configured to engage the longitudinal opening in the sleeve; and
        a second guide including a longitudinal hole, the second guide configured to engage the longitudinal hole of the first guide;
    positioning the alignment body of the alignment guide relative to the implant;
    securing the alignment body to the implant;
    inserting the first guide of the alignment guide into a portion of the alignment body;
    inserting the drill through the first guide to ream the opening in the joint space of the patient's hind foot;
    removing the drill and first guide from the alignment body;
    inserting the shaft through a portion of the alignment body, through the at least two portions of bone, and into the reamed opening in the patient's hind foot; and
    disassembling the alignment guide.

3. The surgical method of claim 2, further comprising:
    inserting a second guide into the first guide of the alignment guide into the alignment body;
    inserting a guide pin through the second guide and the patient's hind foot to intersect the implant;
    removing the second guide from the alignment body;
    inserting the drill over the guide pin to ream the opening in the patient's hind foot;
    inserting the shaft over the guide pin, through the alignment body, and into the patient's hind foot;
    removing the guide pin;
    checking the position of the implant after insertion with an imaging technique; and
    confirming fixation of the patient's hind foot after the shaft is inserted and coupled to the implant.

4. The surgical method of claim 2, wherein the implant further includes a longitudinal opening and at least one hole extending into the exterior surface and into the longitudinal opening;
    wherein the shaft includes a first end with a head portion, a second end with an engagement member, and a hole extending along a longitudinal axis; and
    wherein the first end of the alignment body is configured to couple to the shaft.

5. The surgical method of claim 4, wherein the alignment guide further comprises:
    a drive tube including a first end, a second end, and a hole extending from the first end to the second end, the second end of the drive tube couples to the proximal end of the implant, and wherein the driver includes a superior end and an inferior end, the inferior end inserted into the hole of the drive tube and couples to the proximal end of the implant;

a knob including an engagement opening, the engagement opening couples to the superior end of the driver; and wherein the second end of the alignment body couples to the drive tube.

6. The surgical method of claim 5, wherein the sleeve is configured to mate with the alignment body to align the engagement member of the shaft with the at least one hole of the implant; and wherein the alignment body comprises:
 a support arm including a first end and a second end;
 an alignment arm including a first end and a second end, the first end configured for coupling to the second end of the support arm; and
 the carriage comprising an engagement channel and a threaded hole, the engagement channel is configured to slidingly move along the alignment arm, and the threaded hole threadingly couples the sleeve.

7. The surgical method of claim 1, wherein the implant further includes a hole along a longitudinal axis and at least one opening extending into the exterior surface and intersecting the hole; and the shaft includes a first end with a head portion, a second end with a coupling mechanism, and an opening along a longitudinal axis;

wherein inserting the shaft into the exterior surface of the implant comprise engaging the coupling mechanism of the shaft with the at least one opening to couple the implant to the shaft.

8. The implant surgical method of claim 7, wherein the implant further includes at least one bushing configured to be insertable into the at least one opening.

9. The surgical method of claim 8, wherein the coupling mechanism of the shaft includes a threaded tip for engaging the at least one bushing.

10. The surgical method of claim 8, wherein the coupling mechanism of the shaft includes a threaded tip adjacent to a compression engagement portion of the shaft.

11. The surgical method of claim 7, wherein the exterior surface of the implant is tapered from the proximal end to the distal end.

12. The surgical method of claim 7, wherein the exterior surface of the implant comprises a plurality of grooves.

13. The surgical method of claim 12, wherein the plurality of grooves are substantially perpendicular to the longitudinal axis of the implant and extend around the circumference of the implant.

14. The surgical method of claim 12, wherein the plurality of grooves are angled relative to the longitudinal axis of the implant.

15. The surgical method of claim 12, wherein the plurality of grooves include a first portion of grooves extending horizontally around the circumference of the implant and a second portion of angled grooves that extend linearly the circumference of the implant.

16. The surgical method of claim 7, wherein the at least one opening includes two openings spaced apart along the longitudinal axis of the implant, the two openings are angled at least 90 degrees relative to each other.

17. The implant surgical method of claim 7, wherein the at least one opening includes three openings spaced apart along the longitudinal axis of the implant, the three openings are angled at least 120 degrees from each other.

18. The surgical method of claim 7, wherein the coupling mechanism of the shaft includes a threaded tip for engaging the at least one opening of the bone implant.

19. The method of claim 1, wherein the shaft is selected from at least one of a compression shaft and a fixation shaft.

* * * * *